United States Patent
Dong et al.

(10) Patent No.: US 7,803,401 B2
(45) Date of Patent: *Sep. 28, 2010

(54) DOSAGE FORM COMPRISING LIQUID FORMULATION

(75) Inventors: Liang-Chang Dong, Sunnyvale, CA (US); Steven Espinal, Mountain View, CA (US); Patrick S. L. Wong, Burlingame, CA (US)

(73) Assignee: Encinal Pharmaceutical Investments, LLC, Reamwood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/589,558

(22) Filed: Oct. 30, 2006

(65) Prior Publication Data

US 2007/0048368 A1    Mar. 1, 2007

Related U.S. Application Data

(63) Continuation of application No. 09/740,191, filed on Dec. 19, 2000, now Pat. No. 7,147,867, which is a continuation of application No. 09/353,702, filed on Jul. 14, 1999, now Pat. No. 6,174,547.

(60) Provisional application No. 60/099,619, filed on Sep. 9, 1998.

(51) Int. Cl.
*A61K 9/48* (2006.01)
*A61K 9/66* (2006.01)

(52) U.S. Cl. ............... 424/451; 424/452; 424/455; 424/463

(58) Field of Classification Search .............. 424/451, 424/452, 455, 463
See application file for complete search history.

(56) References Cited

U.S. PATENT DOCUMENTS

| 3,173,867 A | 3/1965 | Zobrist |
| 3,276,586 A | 10/1966 | Rosaen |
| 3,541,005 A | 11/1970 | Strathmann et al. |
| 3,541,006 A | 11/1970 | Bixler et al |
| 3,546,142 A | 12/1970 | Michaels et al. |
| 3,845,770 A | 11/1974 | Theeuwes et al. |
| 3,916,899 A | 11/1975 | Theeuwes et al. |
| 4,034,758 A | 7/1977 | Theeuwes |

(Continued)

FOREIGN PATENT DOCUMENTS

CH    580 961    10/1976

(Continued)

OTHER PUBLICATIONS

Encyclopedia of polymer science and technology, vol. 3, pp. 325-354, 1965.

(Continued)

*Primary Examiner*—Humera N Sheikh
(74) *Attorney, Agent, or Firm*—Morrison & Foerster LLP

(57) ABSTRACT

A sustained release dosage form includes a capsule made of a thermoplastic polymer having a softening point below 200° C. and an orifice formed or formable within the capsule, an emulsion formulation contained within the capsule, and an expandable composition within the capsule remote from the orifice. The emulsion formulation comprises a drug, an emulsifying surfactant, and an oil. The expandable composition is configured to expand and expel the emulsion formulation through the orifice.

17 Claims, 13 Drawing Sheets

U.S. PATENT DOCUMENTS

| | | |
|---|---|---|
| 4,077,407 A | 3/1978 | Theeuwes et al. |
| 4,111,201 A | 9/1978 | Theeuwes et al. |
| 4,160,020 A | 7/1979 | Ayer et al. |
| 4,256,108 A | 3/1981 | Theeuwes |
| 4,259,323 A | 3/1981 | Ranucci |
| 4,663,148 A | 5/1987 | Eckenhoff et al. |
| 4,800,056 A | 1/1989 | Eckenhoff |
| 4,957,494 A | 9/1990 | Wong et al. |
| 5,324,280 A * | 6/1994 | Wong et al. .............. 604/892.1 |
| 5,444,041 A | 8/1995 | Owen |
| 5,614,578 A | 3/1997 | Dong et al. |
| 5,620,705 A | 4/1997 | Dong et al. |
| 5,652,212 A | 7/1997 | Cavanak |
| 5,897,876 A | 4/1999 | Rudnic et al. |
| 6,174,547 B1 | 1/2001 | Dong et al. |
| 6,458,373 B1 * | 10/2002 | Lambert et al. ............. 424/405 |

FOREIGN PATENT DOCUMENTS

| | | |
|---|---|---|
| WO | WO 91/15196 | 10/1991 |

OTHER PUBLICATIONS

Pharmaceutical sciences by Remington, 17th edition, pp. 403-405, (1985).

Van Nostrand Reinhold Encyclopedia of Chemistry, 4th edition, Considine and Considine, editors, pp. 644-645, 1984.

* cited by examiner

Pharmacokinetic Data for Oral Progesterone
Formulations Dosed to Dogs (40mg)

| Formulation # | T$_{max}$(h) | | | | C$_{max}$(ng/ml) | | | | AUC (ng/ml*h) | | | | *Relative BA % Average (s.d) |
|---|---|---|---|---|---|---|---|---|---|---|---|---|---|
| | Dog 1 | 2 | 3 | Avg | Dog 1 | 2 | 3 | Avg (s.d) | Dog 1 | 2 | 3 | Avg (s.d) | |
| 1 | 1 | 1 | 1 | 1 | 38.4 | 13.9 | 24.4 | 25.6(12.3) | 104 | 51 | 104 | 87.2(76.4) | 100 |
| 2 | 0.25 | 0.50 | 0.25 | 0.33 | 252 | 90.8 | 248 | 197(92) | 226 | 113 | 265 | | 232 (21) |
| 3 | 0.50 | 0.25 | 0.50 | 0.42 | 53.4 | 57.7 | 33.7 | 48.3(12.8) | 109 | 95 | 102 | | 130 (50) |
| 4 | 0.5 | 1 | 1 | 0.83 | 174 | 57.1 | 30.4 | 87.2(76.4) | 167 | 289 | 73 | | 176(108) |
| 5 | 0.5 | 1 | 0.25 | 0.58 | 57.2 | 70.8 | 74.7 | 67.5(9.1) | 114 | 342 | 86 | | 181(141) |

AUC is calculated by trapezoidal rule from time zero to the last blood sampling point (12h).
The relative bioavailability is the ratio of AUC for liquid formulations to that for laqueus drug-layer formulation.

Formulation Composition (wt%)

| Components | Formulation # | | | | |
|---|---|---|---|---|---|
| | 1 | 2 | 3 | 4 | 5 |
| Progesterone | 60 | 4 | 4 | 4 | 4 |
| Mannitol | 21 | | | | |
| Ac-di-sol | 10 | | | | |
| Myji 52-s | 5 | | | | |
| HPMC E-5 | 3 | | | | |
| Mg stearate | 1 | | | | |
| Cremophor EL | | 48 | 96 | | 48 |
| Myvacet 9-45 | | 48 | | 96 | |
| Olive oil | | | | | 48 |

FIG. 14

Pharmacokinetic Data for Emulsion Progesterone Formulation and
Nonemulsion Push-Pill Drug-Layer Formulation (300mg dose)

| Formulation # | $T_{max}$(h) | | | | $C_{max}$(ng/ml) | | | | AUC (ng/ml*h) | | | | Relative BA (%) |
|---|---|---|---|---|---|---|---|---|---|---|---|---|---|
| | Dog 1 | 2 | 3 | Avg | Dog 1 | 2 | 3 | Avg (s.d) | Dog 1 | 2 | 3 | Avg (s.d) | Average (s.d) |
| Nonemulsion | 2 | 1 | 1 | 1.33 | 489 | 778 | 649 | 639(145) | 1101 | 1715 | 898 | 1238(425) | 100 |
| Emulsion | 1 | 1 | 1 | 1 | 4800 | 3420 | 5180 | 4467(926) | 7715 | 4708 | 7418 | 6614(1657) | 600 (289) |

AUC is calculated by trapezoidal rule from time zero to the last blood sampling point (12h).
The relative bioavailability is the ratio of AUC for liquid formulations to that for MPA-22 drug-layer formulation.

Formulation Composition (wt%)

| Components | Nonemulsion Drug-Layer | Emulsion Oral Formulation |
|---|---|---|
| Progesterone | 60 | 50 |
| Mannitol | 21 | |
| Ac-di-sol | 10 | |
| Myji S2-s | 5 | 12.5 |
| HPMC E-5 | 3 | |
| Mg stearate | 1 | |
| Cremophor EL | | 25.0 |
| Myvacet 9-45 | | 12.5 |

FIG. 15

DOSAGE FORM COMPRISING LIQUID FORMULATION

CROSS-REFERENCE TO RELATED APPLICATION

This application is a continuation of U.S. application Ser. No. 09/740,191, filed Dec. 19, 2000, published under U.S. Patent Application Publication No. 2001/0001280, which is a continuation of U.S. application Ser. No. 09/353,702, filed Jul. 14, 1999, now U.S. Pat. No. 6,174,547, which claims benefit of U.S. Provisional Application No. 60/099,619, filed Sep. 9, 1998, under 35 U.S.C. §119(e). The content of these applications are incorporated herein by reference.

FIELD OF THE INVENTION

The present invention pertains to a dosage form comprising a liquid formulation comprising a drug. More particularly, the invention concerns a dosage form comprising a liquid formulation comprising a drug that can self-emulsify to enhance the solubility, the dissolution, and the bioavailability of the drug. The invention concerns also a method of enhancing the therapeutic effect of a drug by using the dosage form of the invention.

BACKGROUND OF THE INVENTION

Many drugs administered by the drug dispensing art possess hydrophobic properties that diminish their bioavailability caused by the slow rate of dissolution and concomitantly diminish their therapeutic effect. This is a serious problem with hydrophobic drugs. For example, the preparation and use of stable aqueous formulations comprising a hydrophobic drug, such as insoluble steroids including cortisone acetate, progesterone, testosterone propionate, estradiol monobenzoate, and the like hydrophobic drugs often leads to unwanted problems. These problems are exemplified by the growth of large crystals that can (1) diminish solubility, dissolution, and bioavailability of a drug; (2) be a source of irritation to a patient; and (3) give rise to mechanical difficulties in attempting to pass large crystals through hypodermic needles and through enteral and parenteral tubes.

It will be appreciated by those versed in the drug dispensing arts that if a dosage form comprising a drug formulation is made available that overcomes the tribulations of the prior art, such a dosage form would have a positive value in the drug dispensing art. Likewise, it will be scientifically self-evident to those versed in the drug delivery art, that if a dosage form is made available that delivers the essentially prescribed dose, such a dosage form would have immediate acceptance in the fields of human and veterinary medicine.

OBJECTS OF THE INVENTION

Accordingly, in view of the above presentation, it is an immediate object of this invention to provide a dosage form for the sustained release and the controlled delivery of a beneficial drug that overcomes the shortcomings associated with the prior art.

Another object of the invention is to provide a dosage form comprising a liquid formulation comprising a drug that can be delivered in a preselected and prescribed dose of drug to a patient in need of therapy.

Another object of the invention is to provide a liquid formulation containing an aqueous insoluble drug that can now be dispensed in a known dose for a therapeutic use.

Another object of the invention is to provide a dosage form comprising a liquid formulation that undergoes conversion to an in situ, self-emulsifying formulation to enhance the oral bioavailability of a drug.

Another object of the invention is to provide a stable emulsion comprising an aqueous insoluble drug that remains relatively free of crystal growth, even after extended periods of time.

Another object of the invention is to provide a liquid formulation that can self-emulsify in situ to an oil-in-water microemulsion and thereby essentially prevent drug particles from aggregation/agglomeration during storage and drug delivery over time.

Another object of the invention is to provide an oil-in-water microemulsion wherein a drug has a higher solubility than in water.

Another object of the invention is to provide a self-emulsifying liquid carrier that enhances bioavailability in vivo of poorly absorbed drugs and is compatible with osmotic dosage forms.

Another object of the invention is to provide a dosage form for delivering in vivo a beneficial drug that is difficult to deliver and now can be delivered by this invention in a therapeutically effective dose over twenty-four hours.

Another object of the invention is to provide a dosage form comprising a capsule coated with a semipermeable that comprises a drug in a microemulsion formulation.

Another object of the invention is to provide an injection-molded dosage form comprising a hydrophobic drug in a microemulsion for delivery at a known rate over a sustained release period.

Other objects, features, aspects and advantages of this invention will be more apparent to those versed in the drug delivery art from the following detailed specification taken in conjunction with the drawings and the accompanying claims.

BRIEF DESCRIPTION OF THE DRAWINGS

The drawing figures, which are not drawn to scale but are set forth to illustrate embodiments of the invention, are as follows:

FIGS. 11 to 15 depict the results of pharmacokinetic studies using the dosage forms of the invention.

In the drawings, and in the specification, like parts in related figures are identified by like numbers. The terms appearing earlier in the specification are defined later in the specification.

DETAILED DESCRIPTION OF THE INVENTION

The term emulsion as used in this specification denotes a two-phase system in which one phase is finely dispersed in the other phase. The term emulsifier, as used by this invention, denotes an agent that can reduce and/or eliminate the surface and the interfacial tension in a two-phase system. The emulsifier agent, as used herein, denotes an agent possessing both hydrophilic and lipophilic groups in the emulsifier agent. The term microemulsion, as used herein, denotes a multicomponent system that exhibits a homogenous single phase in which quantities of a drug can be solubilized. Typically, a microemulsion can be recognized and distinguished from ordinary emulsions in that the microemulsion is more stable and usually substantially transparent. The term solution, as used herein, indicates a chemically and physically homogeneous mixture of two or more substances. The term solubility, as used herein, denotes a solid brought into contact with a liquid, whereby molecules of the solid establish an equilibrium with the liquid leaving the solid and returning to it. The term slightly soluble, as used herein, denotes 100 to 1,000 parts of solvent for 1 part of solute, very slightly soluble from 1,000 to 10,000 parts of solvent for 1 part of solute, and practically insoluble, or insoluble, denotes more than 10,000 parts of solvent to 1 part of solvent. The term dissolution denotes a process by which a solid solute enters into solution. The term bioavailability indicates the amount of drug that reaches the general blood circulation from an administered dosage form.

Figure 1:
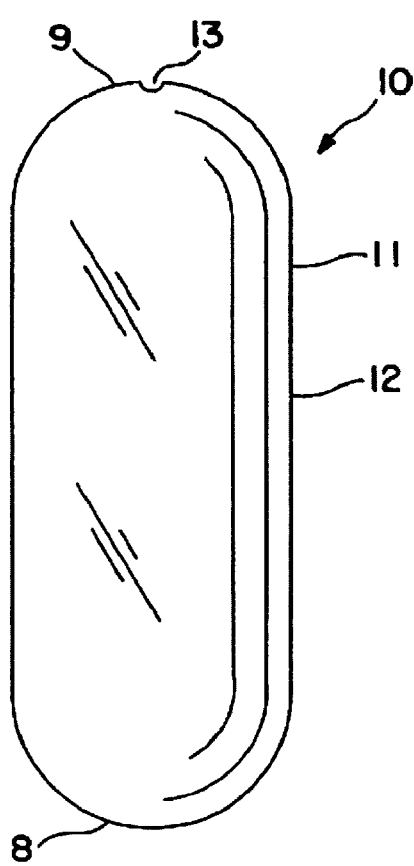
FIG. 1 is a closed, general view of a dosage form provided by the invention.

Turning now to the drawings in detail, which drawings are examples of various dosage forms provided by the invention, and which examples are not to be construed as limiting, one example of a dosage form is seen in FIG. 1. In FIG. 1, a dosage form 10 is seen in closed view comprising a body member 11, comprising a wall 12 that surrounds an internal compartment or space, not shown. Dosage form 10 comprises a lead end 9 with an orifice 13 and a bottom end 8.

Figure 2:
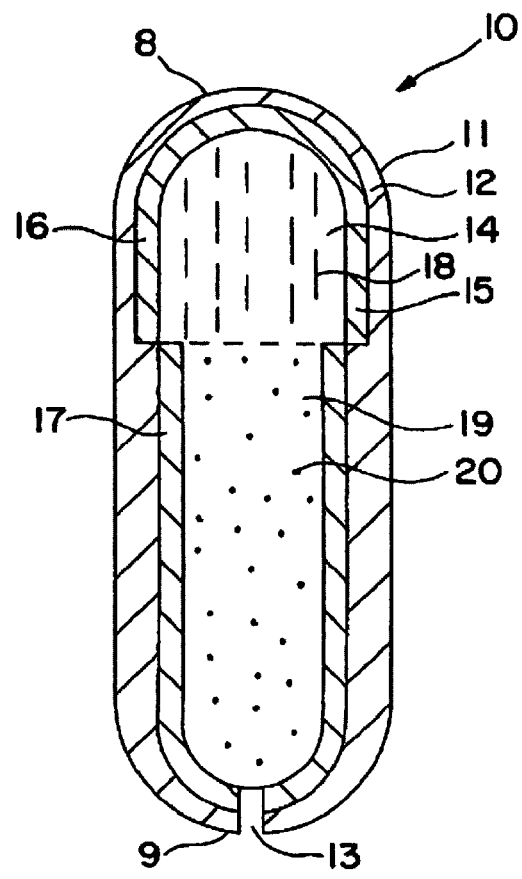
FIG. 2 is an opened view of the dosage form of FIG. 1, wherein the dosage from comprises a capsule made of two parts consisting of a body portion and a cap portion, which capsule contains a drug emulsion formulation and an expandable composition.

In FIG. 2, dosage form 10 comprises body member 11 comprising a wall 12 that surrounds and forms an internal compartment or space 14. Wall 12 comprises an orifice 13 that communicates with the internal compartment 14. A capsule 15 is enclosed in internal compartment 14. Capsule 15 is comprised of two parts, a cap 16 and a receiving body 17, which are fitted together after the larger body portion is filled first with a drug emulsion formulation 19 and then a push displacement layer 18.

Capsule 15 is composed of two sections that are fitted together by slipping or telescoping the cap section over the body section, thus completely surrounding and encapsulating the emulsion formulation. Hard capsules are made by dipping stainless steel molds into a bath containing a solution of a capsule lamina-forming material to coat the mold with the material. Then, the molds are withdrawn, cooled, and dried in a current of air. The capsule is stripped from the mold and trimmed to yield a lamina member with an internal lumen. The engaging cap that telescopically caps the formulation receiving body is made in a similar manner. Then, the closed and filled capsule is capsuled with a semipermeable lamina. The semipermeable lamina can be applied to capsule parts before or after the parts are joined into the final capsule. In another embodiment, the hard capsules can be made with each part having matched locking rings near their opened end that permit joining and locking together the overlapping cap and body after filling with formulation. In this embodiment, a pair of matched locking rings are formed into the cap portion and the body portion, and these rings provide the locking means for securely holding together the capsule. The capsule can be manually filled with the formulation, or they can be machine filled with the formulation. In the final manufacture, the hard capsule is capsuled with a semipermeable lamina permeable to the passage of fluid and substantially impermeable to the passage of useful agent as described hereafter.

Capsule 15, distant from orifice 13, contains an expandable composition 18, initially in contact with the end of capsule 15. Expandable composition 18 is a push-driving force that acts in cooperation with dosage form 10 and capsule 15 for delivering a drug 20 in emulsion formulation 19 from dosage 10. Composition 18 exhibits fluid imbibing and/or absorbing properties. Composition 18 comprises a hydrophilic polymer that can interact with water and aqueous biological fluids and then swell or expand. The hydrophilic polymers are known also as osmopolymers, osmogels, and hydrogels, and they exhibit a concentration gradient across wall 12, whereby they imbibe fluid into dosage form 10. Representative of hydrophilic polymers are poly(alkylene oxide) of 1,000,000 to 10,000,000 weight average molecular weight including poly(ethylene oxide), and an alkali carboxymethylcellulose of 10,000 to 6,000,000 weight average molecular weight including sodium carboxymethylcellulose. Composition 18 may comprise 10 mg to 425 mg of osmopolymer. Composition 18 comprises 1 to 50 mg of a poly(cellulose) of a member selected from the group consisting of hydroxyethylcellulose, hydroxypropylcellulose, hydroxypropylmethylcellulose, and hydroxypropylbutylcellulose. Composition 18 comprises 0.5 mg to 75 mg of an osmotically effective solute, known also as osmotic solute and osmagent, that imbibe fluid through wall 12 into dosage form 10. The osmotically effective solutes are selected from the group consisting of a salt, acid, amine, ester and carbohydrate selected from the group consisting of magnesium sulfate, magnesium chloride, potassium sulfate, sodium sulfate, lithium sulfate, potassium acid phosphate, mannitol, urea, inositol, magnesium succinate, tartaric acid, sodium chloride, potassium chloride, and carbohydrates such as raffinose, sucrose, glucose, lactose, and sorbitol. Composition 18 optionally comprise 0 wt % to 3.5 wt % of a colorant, such as ferric oxide. The total weight of all components in composition 18 is equal to 100 wt %.

The emulsion formulation comprises 100 mg to 1500 mg, or 0.5 wt % to 65 wt %, of a drug 20. Representative drugs include a progestin or an estrogen such as a progestogenic steroid selected from the group consisting of progesterone, norethindrone, levonorgestrel, norgestimate, northindrone, and 17-hydroxyprogesterone; an estrogenic steroid selected from the group consisting of estradiol, estradiol valerate, estradiol benzoate, ethinyl estradiol, estrone, estrone acetate, estriol, and estriol triacetate; representative of additional drugs that are very slightly soluble or practically insoluble in water that can be delivered by the dosage form of this invention comprises diphenidol, meclizine, prochloperazine maleate, anisidione, diphenadione, erythrityl tetranitrate, dizoxin, isoflurophate, reserpine, acetazolamide, methazolamide, bendroflumethiazide, clorpropamide, tolazamide, phenaglycodol, allopurinol, aluminum aspirin, metholrexate, acetyl sulfisoxazole, enitabas, flutamide, cyclosporine, risperidone, fluniside, budesonide, lovastatin, simvastatin, etopside, triamcinolone, famotidine, cisapride, and erythromycin.

The invention is operable for the delivery also of pharmacologically active peptides, protein anabolic hormones, growth promoting hormones, endocrine system hormones, procine growth hormones, bovine growth promoting hormone, equine growth promoting hormone, ovine growth promoting hormone, human growth promoting hormone, hormones derived from the pituitary and hypothalmus glands, recombinant DNA, somatropin, somatotropin, gonadotropic releasing hormone, follicle stimulating hormone, luteinizing hormone, LH-RH, insulin, colchicine, chlorionic gonadotropin, oxytocin, vasopressin, desmopressin, adrenocorticotrophic hormone, prolactin, cosyntropin, bypressin, thyroid stimulating hormone, secretin, pancreozymin, enkephalin, glucagon, and like drugs. The drugs are known to the medical art in U.S. Pat. No. 4,111,201 issued to Theeuwes and in U.S. Pat. No. 4,957,494 issued to Wong, Theeuwes and Eckenhoff.

The emulsion formulation comprises 0.5 wt % to 99 wt % of a surfactant. The surfactant functions to prevent aggregation, reduce interfacial tension between constituents, enhance the free-flow of constituents, and lessen the incidence of constituent retention in the dosage form. The therapeutic emulsion formulation of this invention comprises a surfactant that imparts emulsification comprising a member selected from the group consisting of polyoxyethylenated castor oil comprising 9 moles of ethylene oxide, polyoxyethylenated castor oil comprising 15 moles of ethylene oxide, polyoxyethylene caster oil comprising 20 moles of ethylene oxide, polyoxyethylenated caster oil comprising 25 moles of ethylene oxide, polyoxyethylenated caster oil comprising 40 moles of ethylene oxide, polyoxyethylenated castor oil comprising 52 moles of ethylene oxide, polyoxyethylenated sorbitan monopalmitate comprising 20 moles of ethylene oxide, polyoxyethylenated sorbitan monostearate comprising 20 moles of ethylene oxide, polyoxyethylenated sorbitan monostearate comprising 4 moles of ethylene oxide, polyoxyethylenated sorbitan tristearate comprising 20 moles of ethylene oxide, polyoxyethylenated sorbitan monostearate comprising 20 moles of ethylene oxide, polyoxyethylenated sorbitan trioleate comprising 20 moles of ethylene oxide, polyoxyethylene lauryl ether, polyoxyethylenated stearic acid comprising 40 moles of ethylene oxide, polyoxyethylenated stearic acid comprising 50 moles of ethylene oxide, polyoxyethylenated stearyl alcohol comprising 2 moles of ethylene oxide, and polyoxyethylenated oleyl alcohol comprising 2 moles of ethylene oxide. The surfactants are available from Atlas Chemical Industries, Wilmington, Del.; Drew Chemical Corp., Boonton, N.J.; and GAF Corp., New York, N.Y.

The drug emulsified formulation of the invention initially comprises an oil phase. The oil phase of the emulsion comprises any pharmaceutically acceptable oil which is immiscible with water. The oil can be an edible liquid such as a non-polar ester of an unsaturated fatty acid, derivatives of such esters, or mixtures of such esters can be utilized for this purpose. The oil can be vegetable, mineral, animal or marine in origin. Examples of non-toxic oils comprise a member selected form the group consisting of peanut oil, cottonseed oil, sesame oil, olive oil, corn oil, almond oil, mineral oil, castor oil, coconut oil, palm oil, cocoa butter, safflower, a mixture of mono- and diglycerides of 16 to 18 carbon atoms, unsaturated fatty acids, fractionated triglycerides derived from coconut oil, fractionated liquid triglycerides derived from short chain 10 to 15 carbon atoms fatty acids, acetylated monoglycerides, acetylated diglycerides, acetylated triglycerides, olein known also as glyceral trioleate, palmitin known as glyceryl tripalmitate, stearin known also as glyceryl tristearate, lauric acid hexylester, oleic acid oleylester, glycolyzed ethoxylated glycerides of natural oils, branched fatty acids with 13 molecules of ethyleneoxide, and oleic acid decylester. The concentration of oil, or oil derivative in the emulsion formulation is 1 wt % to 40 wt %, with the wt % of all constituents in the emulsion preparation equal to 100 wt %. The oils are disclosed in Pharmaceutical Sciences by Remington, $17^{th}$ Ed., pp. 403-405, (1985) published by Mark Publishing Co., in Encyclopedia of Chemistry, by Van Nostrand Reinhold, $4^{th}$ Ed., pp. 644-645, (1984) published by Van Nostrand Reinhold Co.; and in U.S. Pat. No. 4,259,323 issued to Ranucci.

Capsule 15, as seen in FIG. 2, is surrounded by a wall 12. Wall 12 comprises a composition permeable to the passage of fluid, aqueous and biological fluid present in the environment of use, in animal including a human, and wall 12 is substantially impermeable to the passage of drug 20, and the components of emulsion formulation 19. Wall 12 is a non-toxic and it maintains its physical and chemical integrity during the drug delivery device of dosage form 10. Representative of materials for forming wall 12 include semipermeable polymers, semipermeable homopolymers, semipermeable copolymers, and semipermeable terpolymers. The polymers comprising wall 12 include cellulose esters, cellulose ethers, and cellulose ester-ethers. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkylsulfamate, and semipermeable polymer forming groups.

The semipermeable materials typically include a member selected from the group consisting of cellulose acylate, cellulose diacylate, cellulose triacetate, cellulose acetate, cellulose diacetate, cellulose triacetate, mono-, di-, and tri-cellulose alkanylates, mono-, di-, and tri-alkenylates, mono-, di-, and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%; and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acette butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, cellulose acetate succinate, cellulose propionate succinate, cellulose acetate octanotate, cellulose valerate palmitate, cellulose acetate heptonate, and the like. Semipermeable polymers are known in U.S. Pat. No. 4,077,407, and they can be made by procedures described in Encyclopedia of Polymer Science and Technology, Vol. 3, pages 325 to 354, 1964, published by Interscience Publishers, Inc., New York.

Additional semipermeable polymers include cellulose acetaldehyde dimethyl acetate; cellulose acetate ethylcarbamate; cellulose acetate methylcarbamate; cellulose dimethylaminoacetate; semipermeable polyamides; semipermeable polyurethanes; semipermeable sulfonated polystyrenes; cross-linked, selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable polystyrene derivatives; semipermeable poly (sodium styrenesulfonate); semipermeable poly(vinylbenzyltrimethyl) ammonium chloride; semipermeable polymers exhibiting a fluid permeability of 10 to 10 (cc. mil/cm.hr.atm) expressed as per atmosphere of hydrostatic or osmotic pressure difference across a semipermeable wall. The polymers are known to the art in U.S. Pat. Nos. 3,845,770; 3,916,899; 3,916,899; and 4,160,020, and in Handbook of Common Polymers, by Scott, J. R. and Roff, W. J., 1971, published by CRC Press, Cleveland, Ohio.

Figure 3:
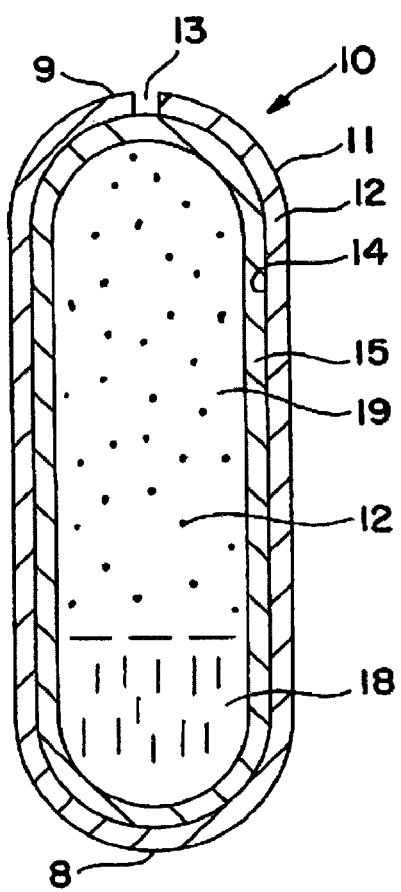
FIG. 3 is an opened view of the dosage form of FIG. 1, wherein the dosage form comprises a capsule made of a single piece and contains a drug emulsion formulation and an expandable composition.

FIG. 3 illustrates another dosage form 10 provided by the invention. In FIG. 3, dosage form 10 comprises a body 11, comprising wall 12, orifice 13, that surrounds internal compartment 14. Internal compartment 14 comprises a one-piece capsule 15. Capsule 15 comprises a pharmaceutical emulsion formulation 19 comprising drug 20 and an expandable composition 18. Capsule 15 is surrounded and/or coated by semipermeable wall 12. The presentation of dosage form 10 in FIG. 2 is referred to and included in this presentation of dosage form 10 in FIG. 3. The one-piece capsule used by the invention can be made by different operations. The one-piece capsule is of a sealed construction encapsulating the drug and the emulsion formulation therein. The capsule is made by various processes including the plate process, the rotary die process, the reciprocating die process, and the continuous process. The plate process uses a set of molds. A warm sheet of a prepared capsule lamina-forming material is laid over the lower mold and the formulation poured on it. A second sheet of the lamina-forming material is placed over the formulation followed by the top mold. The mold set is placed under a press and a pressure applied, with or without heat to form a unit, capsule. The capsules are washed with a solvent for removing excess agent formulation from the exterior of the capsule, and the air-dried capsule is capsuled with a semipermeable wall.

The rotary die process uses two continuous films of capsule lamina-forming material that are brought into convergence between a pair of revolving dies and an injector wedge. The process fills and seals the capsule in dual and coincident operations. In this process, the sheets of capsule lamina-forming material are fed over guide rolls, and then down between the wedge injector and the die rolls. The agent formulation to be capsuled flows by gravity into a positive displacement pump. The pump meters the agent formulation through the wedge injector and into the sheets between the die rolls. The bottom of the wedge contains small orifices lined up with the die pockets of the die rolls. The capsule is about half-sealed when the pressure of pumped agent formulation forces the sheets into the die pockets, wherein the capsules are simultaneously filled, shaped, hermetically sealed and cut from the sheets of lamina-forming materials. The sealing of the capsule is achieved by mechanical pressure on the die rolls and by heating of the sheets of lamina-forming materials by the wedge. After manufacture, the agent formulation-filled capsules are dried in the presence of forced air, and a semipermeable lamina capsuled thereto, by processes described hereafter.

The reciprocating die process produces capsules by leading two films of capsule lamina-forming material between a set of vertical dies. The dies as they close, open, and close perform as a continuous vertical plate forming row after row of pockets across the film. The pockets are filled with agent formulation, and as the pockets move through the dies, they are sealed, shaped, and cut from the moving film as capsules filled with agent formulation. A semipermeable capsulating lamina is coated thereon to yield the capsule. The continuous process is a manufacturing system that also uses rotary dies, with the added feature that the process can successfully fill active agent in dry powder form into a soft capsule, in addition to encapsulating liquids. The filled capsule of the continuous process is encapsulated with a semipermeable polymeric material to yield the capsule. FIG. 3 shows the expandable composition which is an osmotic engine and the emulsion formulation in the soft gelatin capsule. Procedures for manufacturing single-piece capsules are disclosed in U.S. Pat. No. 4,627,850, issued to inventors Deters, Theeuwes, Mullins and Eckenhoff.

Figure 4:
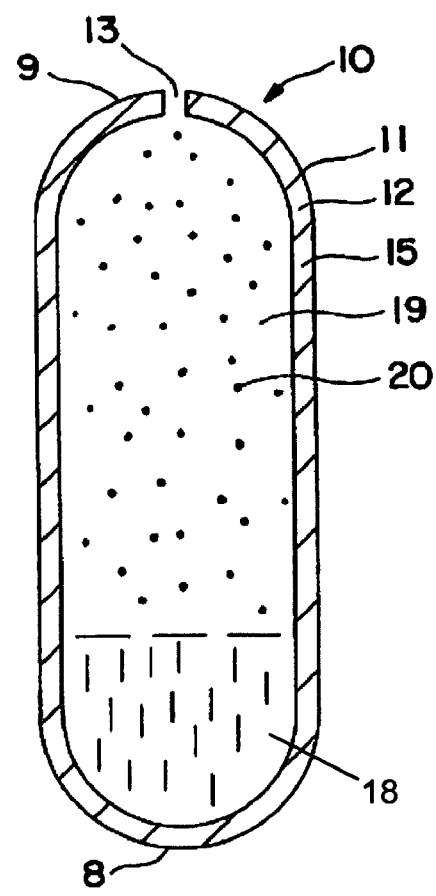
FIG. 4 is an opened view of the dosage form of FIG. 1, formed by injection-molding as a single piece and comprises a drug emulsion formulation and an expandable composition.

FIG. 4 illustrates another dosage form 10 provided by the invention. In FIG. 4, dosage form 10 comprises body 11, wall 12, orifice 13, made as capsule 15 comprising an internal emulsion formulation 19 comprising drug 20. Capsule 15 comprises an expandable composition 18. The presentation of the parts identified by numbers as discussed above is incorporated in the disclosure of drawing FIG. 4.

In FIG. 4, dosage form 10, which is in this manufacture of capsule 15, is made from an injection-moldable composition by an injection-molding technique. Injection-moldable compositions provided for injection-molding into wall 12 comprise a thermoplastic polymer, or the compositions comprise a mixture of thermoplastic polymers and optional injection-molding ingredients. The thermoplastic polymer that can be used for the present purpose comprise polymers that have a low softening point, for example, below 200° C., preferably within the range of 40° C. to 180° C. The polymers are preferably synthetic resins, addition polymerized resins, such as polyamides, resins obtained from diepoxides and primary alkanolamines, resins of glycerine and phthalic anhydrides, polymethane, polyvinyl resins, polymer resins with end-positions free or esterified carboxyl or caboxamide groups, for example with acrylic acid, acrylic amide, or acrylic acid esters, polycaprolactone, and its copolymers with dilactide, diglycolide, valerolactone and decalactone, a resin composition comprising polycaprolactone and polyalkylene oxide, and a resin composition comprising polycaprolactone, a polyalkylene oxide such as polyethylene oxide, poly(cellulose) such as poly(hydroxypropylmethylcellulose), poly(hydroxyethylmethylcellulose), and poly(hydroxypropylcellulose). The membrane forming composition can comprise optional membrane-forming ingredients such as polyethylene glycol, talcum, polyvinylalcohol, lactose, or polyvinyl pyrrolidone. The compositions for forming an injection-molding polymer composition can comprise 100% thermoplastic polymer. The composition in another embodiment comprises 10% to 99% of a thermoplastic polymer and 1% to 90% of a different polymer with the total equal to 100%. The invention provides also a thermoplastic polymer composition comprising 1% to 98% of a first thermoplastic polymer, 1% to 90% of a different, second polymer and 1% to 90% of a different, third polymer with all polymers equal to 100%. Representation composition comprises 20% to 90% of thermoplastic polycaprolactone and 10% to 80% of poly(alkylene oxide); a composition comprising 20% to 90% polycaprolactone and 10% to 60% of poly(ethylene oxide) with the ingredients equal to 100%; a composition comprising 10% to 97% of polycaprolactone, 10% to 97% poly(alkylene oxide), and 1% to 97% of poly(ethylene glycol) with all ingredients equal to 100%; a composition comprising 20% to 90% polycaprolactone and 10% to 80% of poly(hydroxypropylcellulose) with all ingredients equal to 100%; and a composition comprising 1% to 90% polycaprolactone, 1% to 90% poly(ethylene oxide), 1% to 90% poly(hydroxypropylcellulose) and 1% to 90% poly(ethylene glycol) with all ingredients equal to 100%. The percent expressed is weight percent, wt %.

In another embodiment of the invention, a composition for injection-molding to provide a membrane is prepared by blending a composition comprising a polycaprolactone 63 wt %, polyethylene oxide 27 wt %, and polyethylene glycol 10 wt % in a conventional mixing machine, such as a MORIYAMA® Mixer at 65° C. to 95° C., with the ingredients added to the mixer in the following sequence, polycaprolactone, polyethylene oxide and polyethylene glycol. All the ingredients were mixed for 135 minutes at a rotor speed of 10 to 20 rpm. Next, the blend is fed to a BAKER PERKINS KNEADER® extruder at 80° C. to 90° C., at a pump speed of 10 rpm and a screw speed of 22 rpm, and then cooled to 10° C. to 12° C., to reach a uniform temperature. Then, the cooled extruded composition is fed to an Albe Pelletizer, converted into pellets at 250° C., and a length of 5 mm. The pellets next are fed into an injection-molding machine, an ARBURG ALLROUNDER® at 200° F. to 350° F. (93° C. to 177° C.), heated to a molten polymeric composition, and the liquid polymer composition forced into a mold cavity at high pressure and speed until the mold is filled and the composition comprising the polymers are solidified into a preselected shape. The parameters for the injection-molding consists of a band temperature through zone 1 to zone 5 of the barrel of 195° F. (91° C.) to 375° F., (191° C.), an injection-molding pressure of 1818 bar, a speed of 55 cm$^3$/s, and a mold temperature of 75° C. The injection-molding compositions and injection-molding procedures are disclosed in U.S. Pat. No. 5,614,578 issued to Dong, Wong, Pollock, and Ferrari.

The expression "orifice," as used herein comprises means and methods suitable for releasing the useful, active drug emulsion formulation from the dosage form. The expression includes passageway, aperture, hole, bore, pore, and the like through the semipermeable wall. The orifice can be formed by mechanical drilling, laser drilling, or by eroding an erodible element, such as a gelatin plug, a pressed glucose plug, by crimping the walls to yield the orifice when the dosage form is in the environment of use. In an embodiment, the orifice in wall 12 is formed in the environment of use in response to the hydrostatic pressure generated in dosage form 10. The orifice 13 can be formed by mechanical rupturing of wall 12 during operation of dosage form 10. A detailed description of orifices and the maximum and minimum dimensions of an orifice are disclosed in U.S. Pat. Nos. 3,845,770 and 3,916,899, both issued to inventors Theeuwes and Higuchi.

EXAMPLES OF THE INVENTION

The following examples are illustrative of the present invention, and the examples should not be considered as limiting the scope of this invention in any way, as these examples and other equivalents thereof will become apparent to those versed in the art in the light of the present disclosure, and the accompanying claims.

Example 1

A dosage form is manufactured for dispensing a beneficial drug, progesterone, to the gastrointestinal tract of a human as follows: first, an expandable composition is prepared in a fluid bed granulator. The expandable composition comprises 30 wt % sodium chloride screened through a 21 mesh screen, added to a granulator bowl, followed by 58.75 wt % sodium carboxymethylcellulose, 5 wt % hydroxypropylmethylcellulose, and 1 wt % red ferric oxide added to the granulator bowl. In a separate mixer, a granulation solution is prepared by dissolving 5 wt % hydroxypropylcellulose in purified water. Next, the granulating solution is sprayed onto the fluidized powders, in the granulated unit, until all the solution is applied and the powders are granular. Next, 0.25 wt % magnesium stearate lubricant is blended with the freshly prepared granules.

Next, the granules are compressed into a tablet-shaped layer comprising 250 mg of the granules, in a 9/32 inch punch, and tamped and then compressed under a force of 1 metric ton.

Next, a drug layer is prepared as follows: first, 50 wt % of microfluidized progesterone, 12.5 wt % polyoxyl 35 castor oil, available as Cremophor EL from BASF Corp., Mount Olive, N.J., and 37.5 wt % acetylated monoglyceride, commercially available as Myvacet from Eastman Chemical Company, Kingsport, Tenn., are mixed homogenously in a homogenizer.

Then, a capsule, made of gelatin, commercial size 0, is separated into its two segments, the body and its cap. First, 600 mg of the drug layer is filled into the gelatin capsule body. Then, the expandable tablet is placed on the top of the drug formulation, and the filled capsule body is closed with the gelatin cap.

Figure 5A:
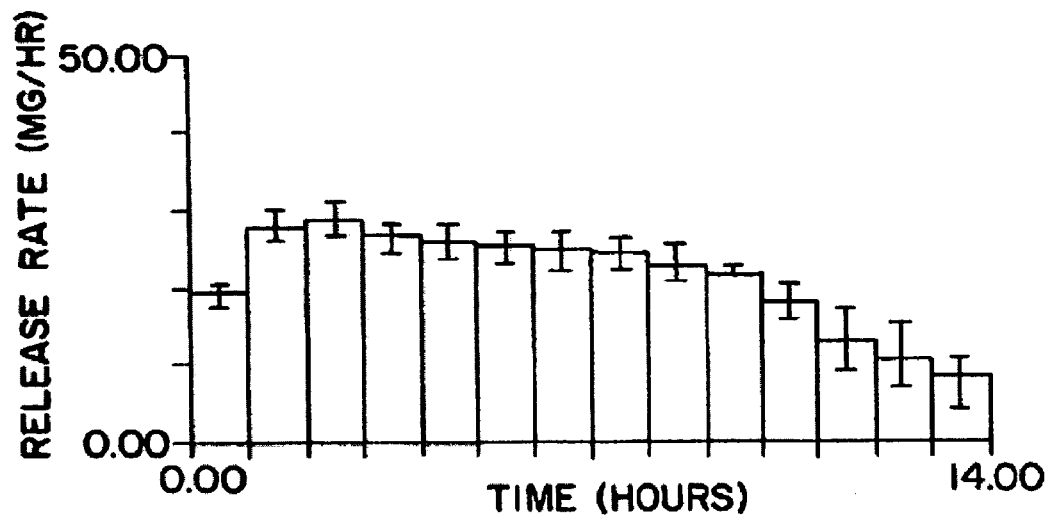
FIGS. 5A and 5B depict release rate and the cumulative amount released from a dosage form.
Figure 5B:
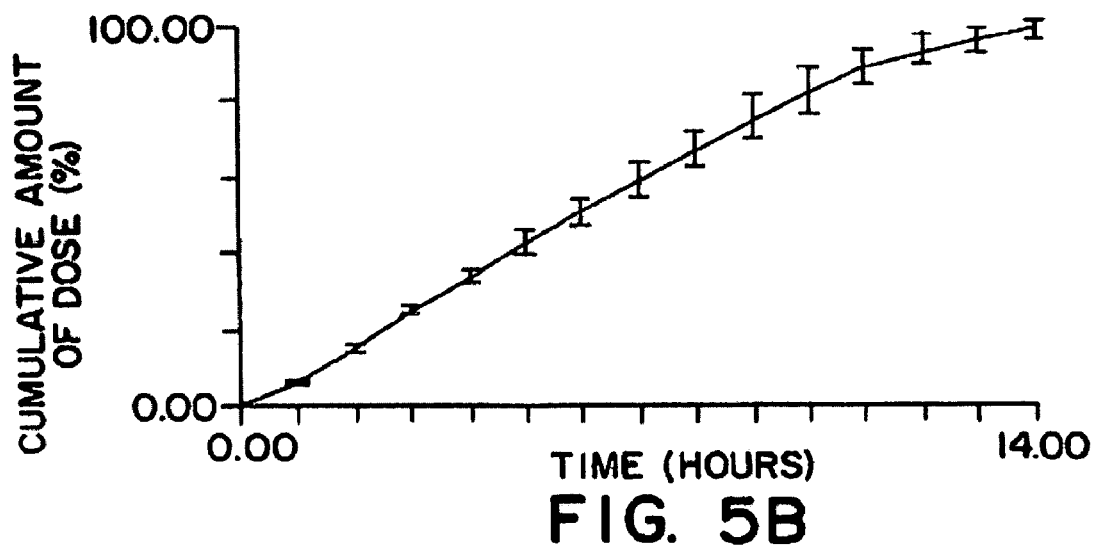

The assembled capsule is coated with a semipermeable wall. The wall-forming composition comprises 85 wt % cellulose acetate comprising a 39.8% acetyl content, and 15 wt % polyethylene glycol 3350. The wall-forming composition is dissolved in acetone/methanol (80/20 wt/wt) cosolvent to make a 4% solid solution. The solution is sprayed onto and around the closed capsule in a coater. After coating, the semipermeable wall coated capsules are dried in an oven at 50° C. and 50° RH (relative humidity) for 1 day, to remove the solvents, and yield the dosage form. An exit is laser drilled through the wall. The dosage form releases 90% of its progesterone in 12 hrs., at a controlled rate, which is exemplified in FIG. 5A and FIG. 5B. The bars represent the minimum and maximum.

Example 2

The procedure of Example 1 is followed with all conditions as set forth, except the drug composition comprises 50 wt % progesterone, 37.5 wt % polyoxyl 35 castor oil, and 12.5 wt % distilled acetylated monoglyceride, commercially available as Myvacet from Eastman Chemical Company, Kingsport, Tenn.

Example 3

The procedure of Example 1 is followed with all conditions as set forth, except the drug composition comprises 50 wt % progesterone, 25 wt % polyoxyl 35 castor oil, and 25 wt % acetylated monoglyceride.

Example 4

The procedure of Example 1 is repeated with all conditions as previously described, except for the drug layer which comprises 50 wt % progesterone, and 50 wt % polyoxyl 35 castor oil.

Figure 6:
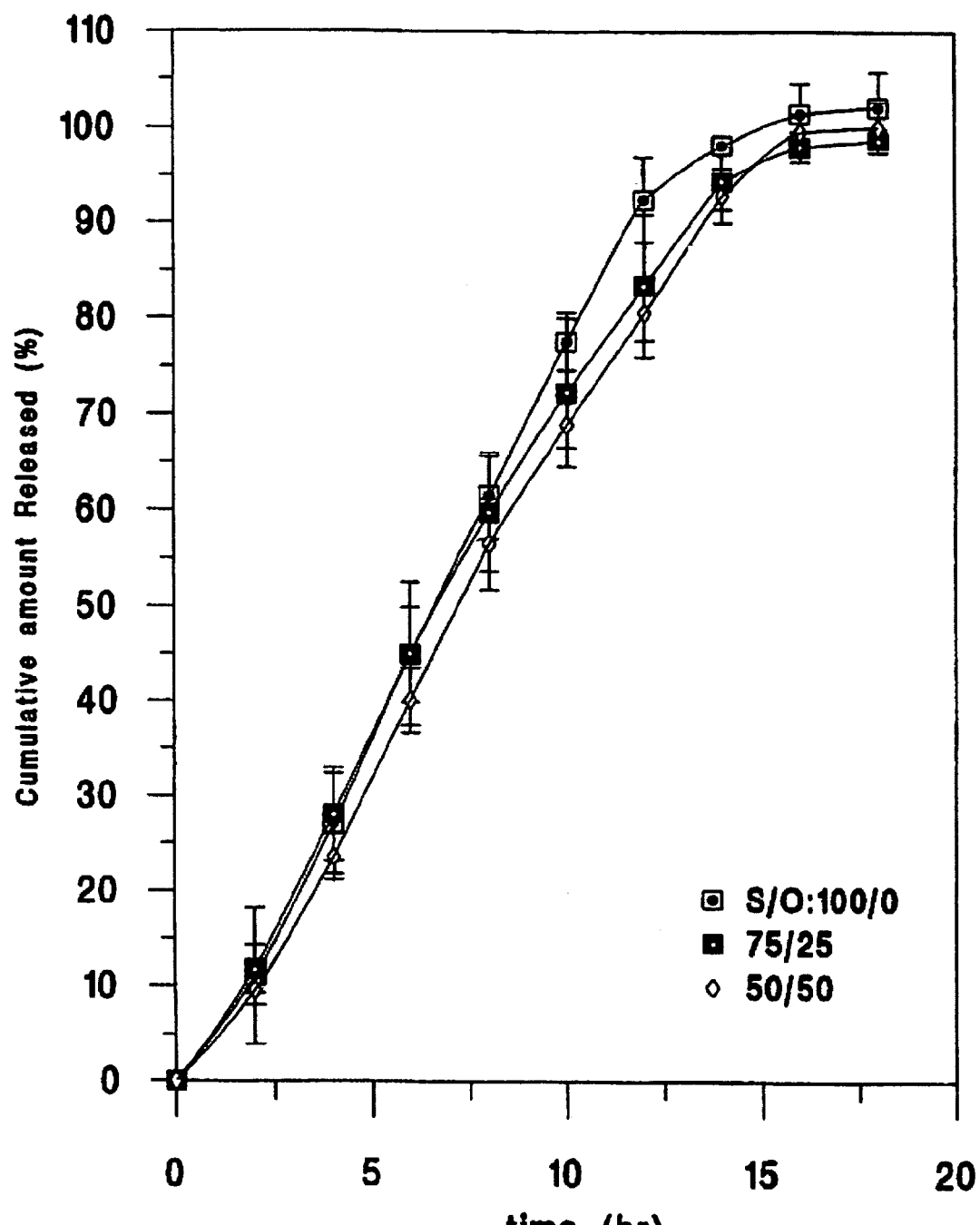
FIG. 6 depicts the cumulative dose released over time.
Figure 7:
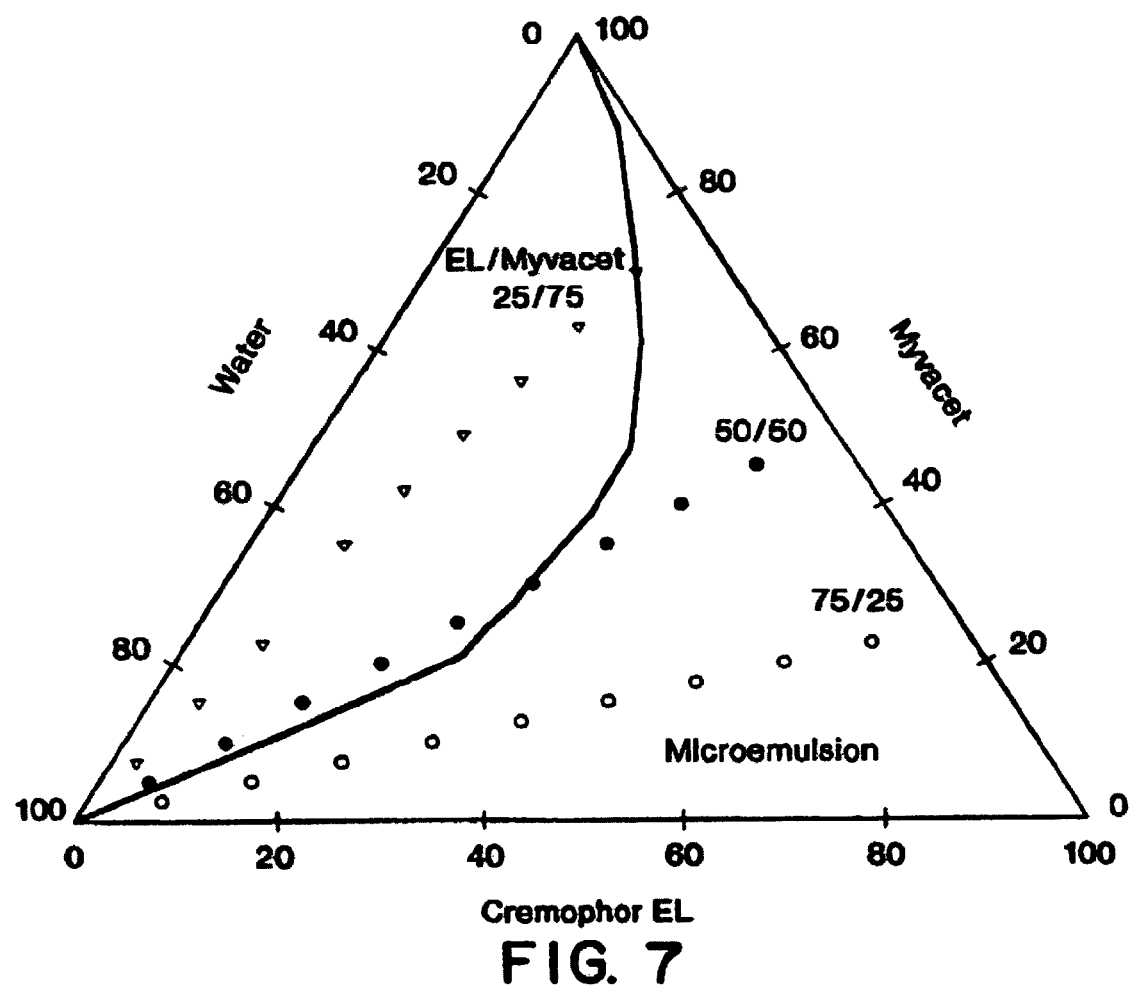
FIG. 7 depicts the a phase diagram for dosage forms provided by the invention.
Figure 8:
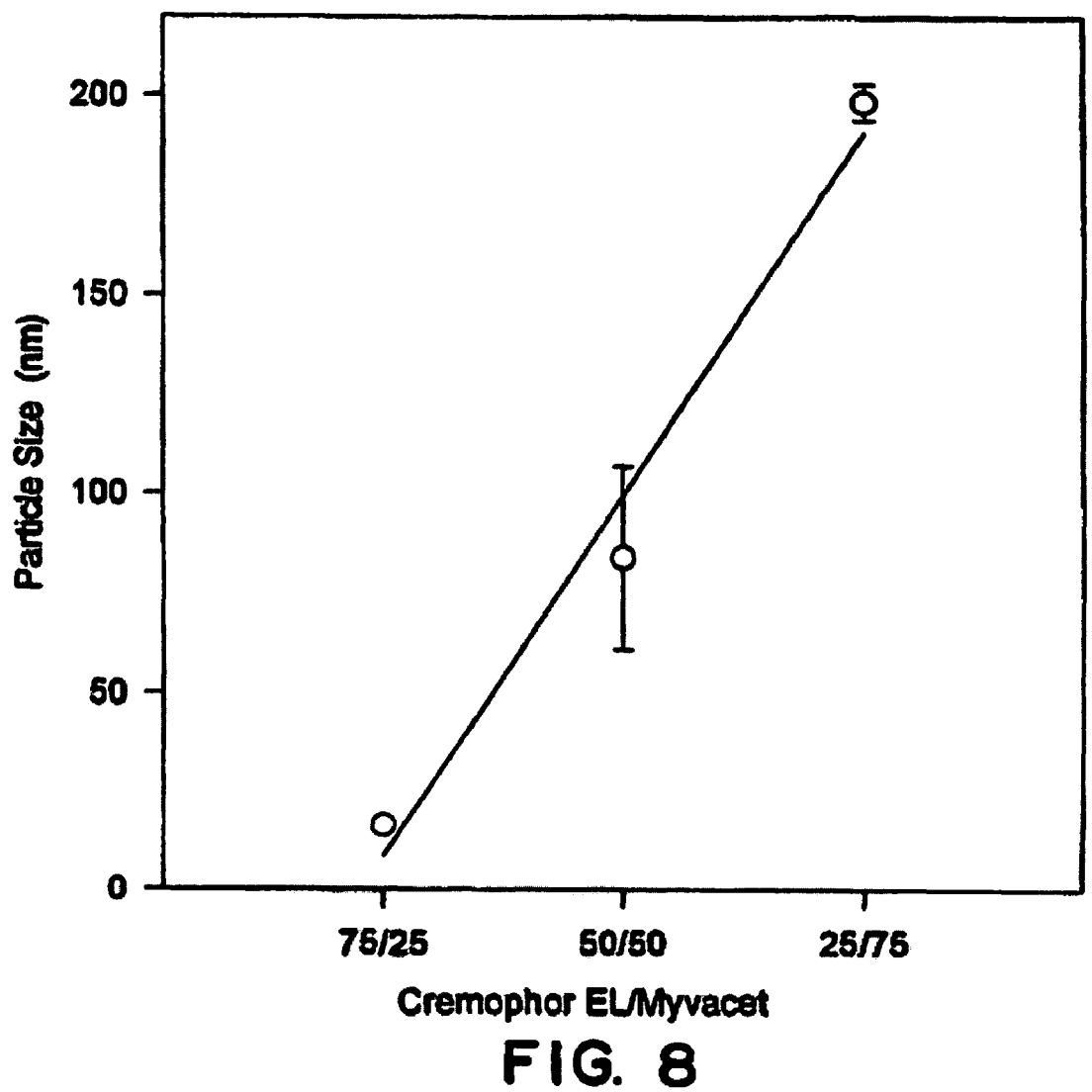
FIG. 8 depicts particle size in a formulation provided by the invention.

The dosage form release rate profile for the dosage form prepared according to Examples 2 to 4 are illustrated in the accompanying drawing. Accompanying FIG. 6 depicts the progesterone release rate of dosage forms with various surfactant/oil ratios. FIG. 7 is a phase diagram comprising three components, Cremophor EL polyoxyl 35 castor oil, Myvacet distilled acetylated monoglyceride, and water, when the self-emulsifying formulation is mixed with water at 37° C. The phase diagram demonstrates that the liquid formulation can self-emulsify in situ to micelles, microemulsion and emulsions depending upon the ratio of the components in the phase diagram. FIG. 8 depicts the correlation between the ratio and the oil droplets size, which is demonstrated by the self-emulsification to microemulsion by the polyoxyl 35 castor oil-distilled acetylated monoglyceride ratio higher than 50/50. In FIG. 8, the following conditions prevailed: Pre-mixed Cremophor EL/Myvacet was added to water and stirred. Particle size was measured using a sub-micro particle size analyzer. Sample intensity was in the required range.

| Cremophor EL/Myvacet | Particle Size, nm | SD | # of Run |
|---|---|---|---|
| 75/25 | 16 | 1 | 2 |
| 50/50 | 84 | 23 | 3 |
| 25/75 | 198 | 5 | 6 |

Figure 9:
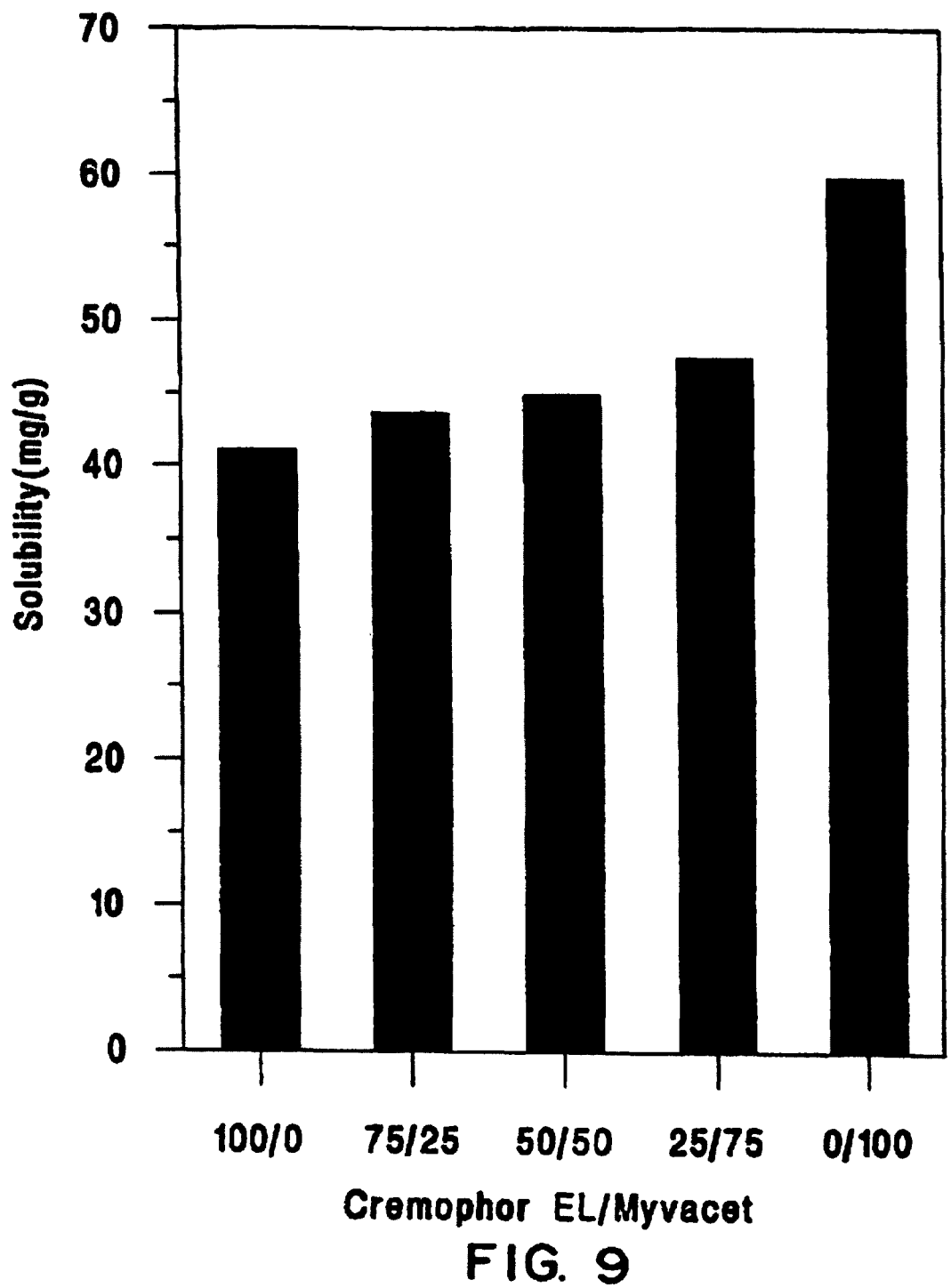
FIG. 9 depicts the solubility of progesterone in components of the invention.
Figure 10:
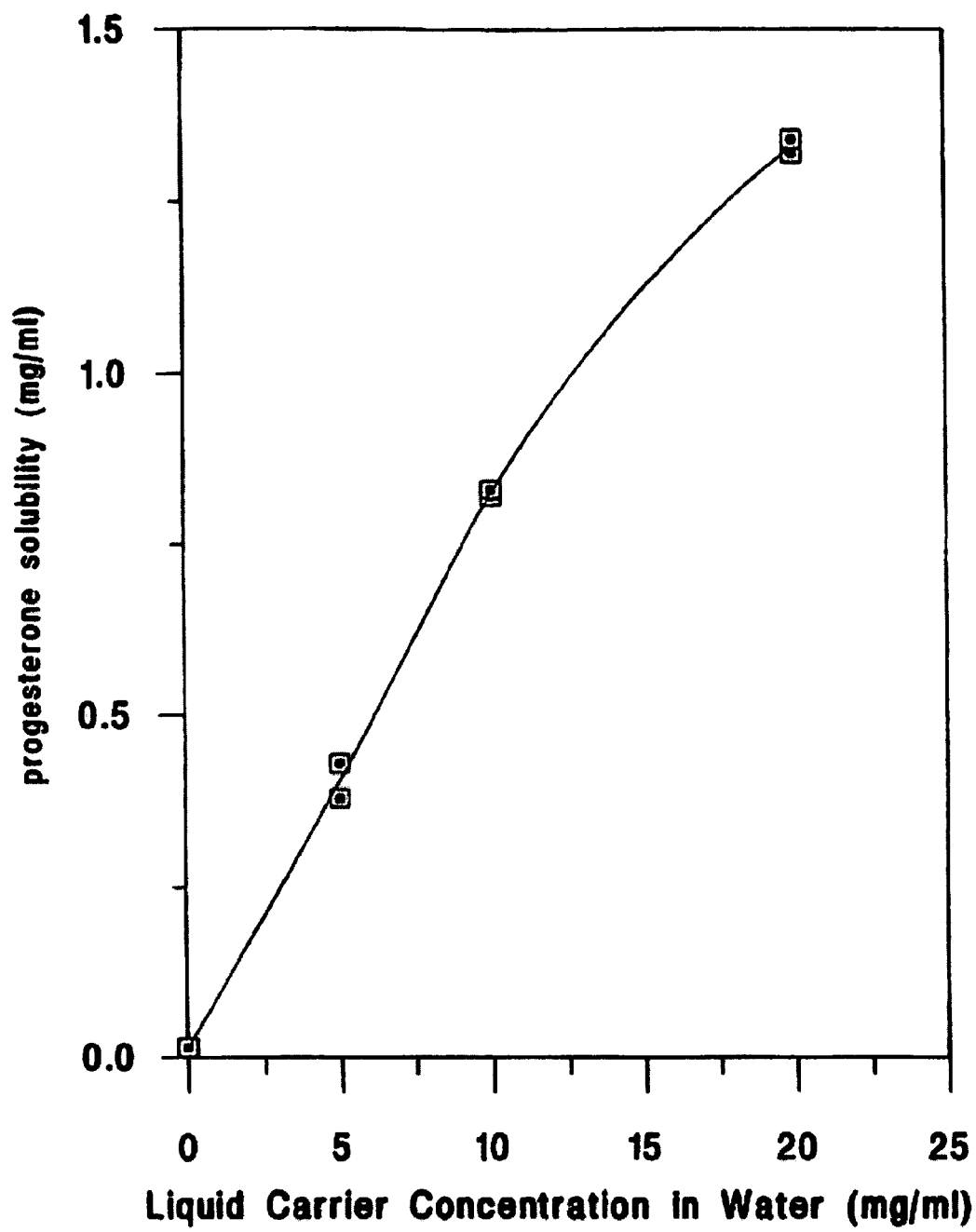
FIG. 10 depicts progesterone solubility in self-emulsified liquid carriers.

In the chart, SD denotes standard deviation and # denotes the number of runs. FIG. 9 is the solubility profile of progesterone in the polyoxyl 35 castor oil and distilled acetylated monoglycerides at various weight ratios. FIG. 10 shows the enhancement of progesterone solubility in water by using liquid carrier comprising polyoxyl 35 castor oil and distilled acetylated monoglyceride.

Example 5

Figure 11:
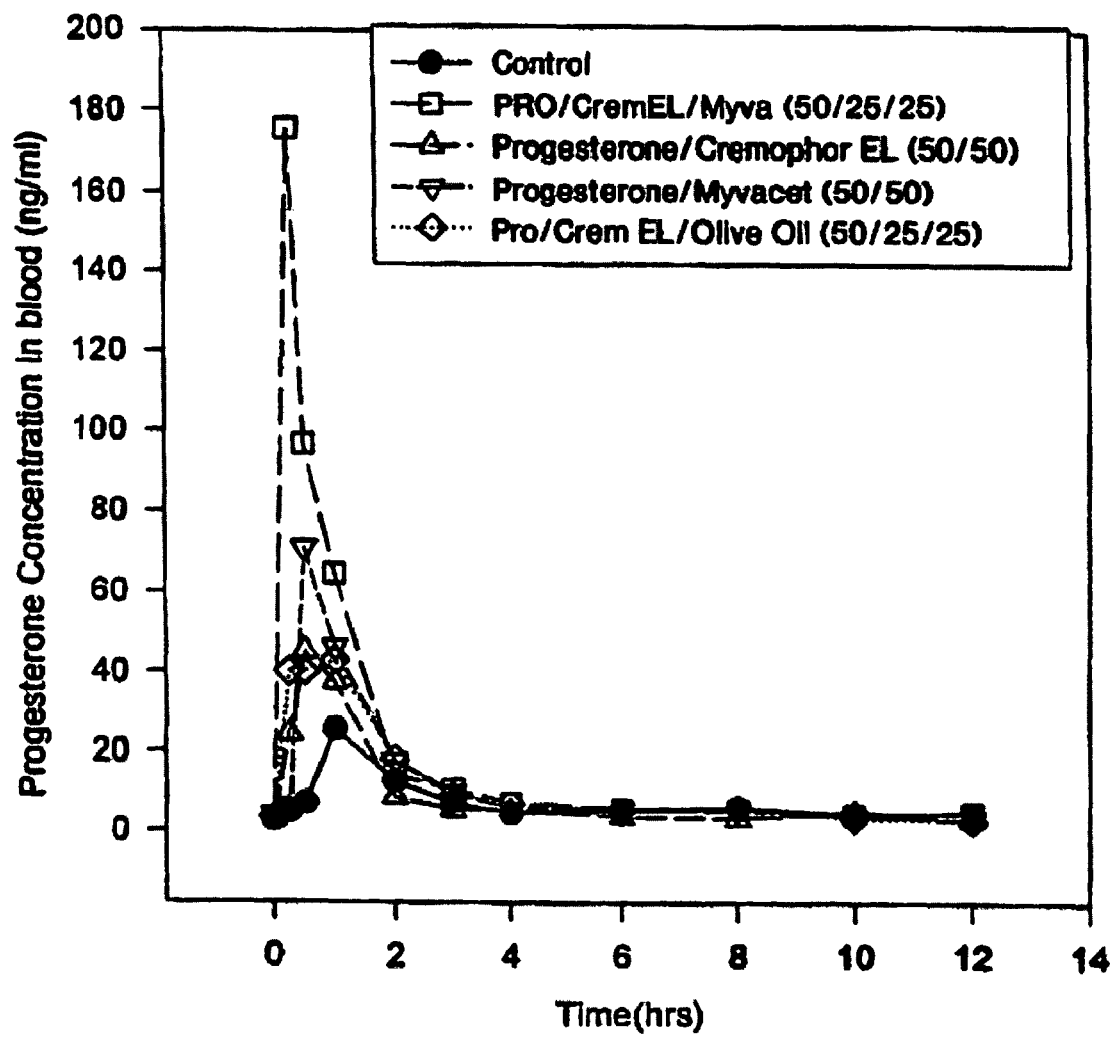
Figure 12:
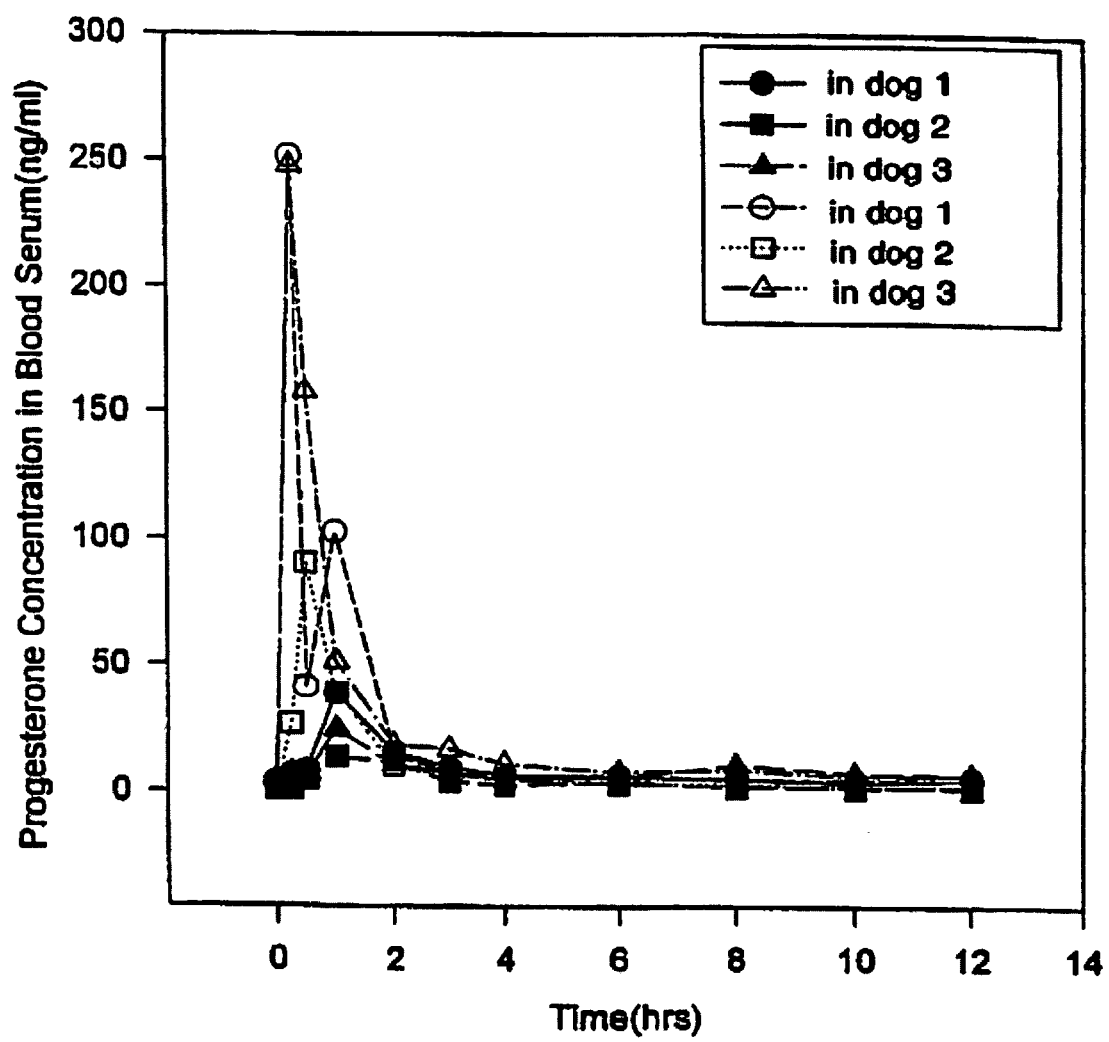
Figure 13:
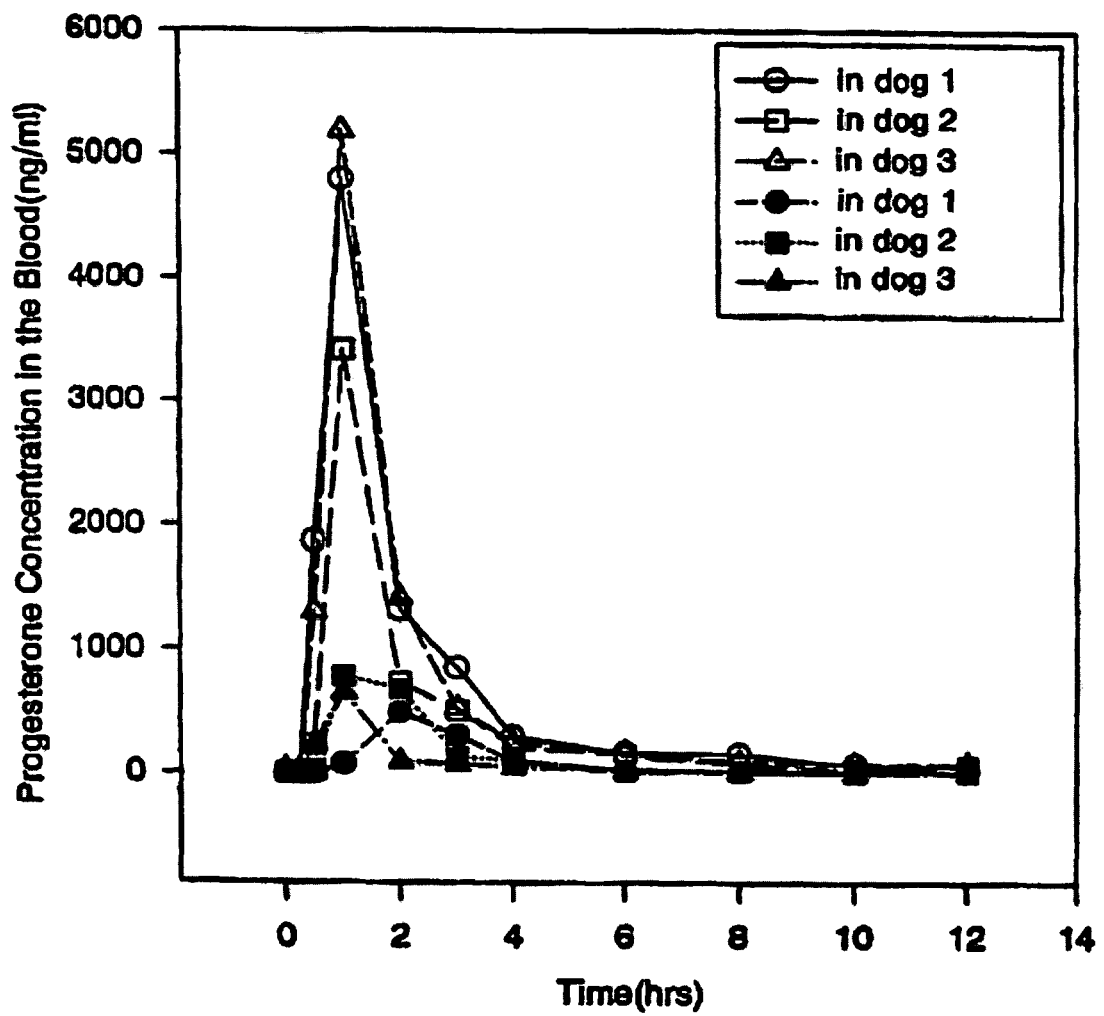

Pharmacokinetic studies were conducted using the dosage form provided by the invention. In this study, dosage forms were administered to canines, wherein the dosage forms comprises 1 g of liquid emulsion formulation containing 40 mg of progesterone. The AUC, area under the curve, as determined by trapezoidal rule from time zero to the last blood sampling point, which is the $12^{th}$ hour. The AUC of the dosage form comprising polyoxyl 35 castor oil and distilled acetylated monoglyceride was 226 ng/ml-h compared to 104 ng/ml-h for the control. The mean C max for the dosage form was 197 ng/ml compared to 25.6 ng/ml for the control. The control was a solid dosage form comprising progesterone in a non-emulsion formulation (#1 formulation). A suspension of 300 mg progesterone in polyoxyl 35 castor oil/distillated acetylated monoglyceride liquid carrier was tested in the study. The results for the liquid carrier of the invention showed a C max of 4467 ng/ml compared to 639 ng/ml for the control. The bioavailability of the dosage form of the invention is about 600% relative to the control. In a previous clinical study, the control formulation showed a bioavailability of 83% relative to a commercial product, Utrogestrin®. The present canine pharmacokinetic study demonstrated the dosage form of this invention with unexpected results and microemulsion formulation of the invention is very effective to enhance the bioavailability of water-insoluble drugs. The results of the study are presented in the accompanying Figures, wherein in FIG. 11, the control denotes a solid dosage form comprising progesterone in a nonemulsion environment; Pro/CremEL/Myva denotes progesterone in a polyoxyl 35 castor oil/distilled acetylated monoglyceride emulsion; wherein (50/25/25) denotes the ratio in the composition, progesterone/Cremophor denotes progesterone formulated with polyoxyl 35 castor oil; progesterone/Myvacet denotes progesterone in distilled acetylated monoglyceride; and Pro/CremEL/Olive Oil denotes progesterone formulated with polyoxyl 35 castor oil/olive oil; FIG. 12 depicts canine studies in six canines for determining the serum progesterone concentration comparing solid control formulation with emulsion formulation where closed symbols represent solid dosage forms each delivering 40 mg of progesterone, and open symbols represent the liquid carrier provided by the invention wherein the carrier comprises 40 mg of progesterone in an emulsion formulation; FIG. 13 depicts the serum concentration comparing the solid control dosage forms with emulsion formulation where closed symbols represent the solid dosage form each delivering 300 mg of progesterone and open symbols represent the emulsion formulation provided by this invention, wherein the emulsion formulation comprise 300 mg of progesterone; FIG. 14 depicts the pharmacokinetic results for oral preparations (40 mg) provided by the invention; and FIG. 15 depicts the pharmacokinetic data for a larger 300 mg study.

METHOD OF USING THE INVENTION

The invention provides a method of administering a drug by orally admitting into the gastrointestinal tract of a human the dosage form of the invention. The method comprises the steps of (1) admitting orally the dosage form into the gastrointestinal tract, which dosage form comprises a wall for imbibing an external aqueous fluid through the wall into the dosage form and surrounds and forms a space comprising a gelatin capsule comprising an emulsifiable formulation comprising a drug, and a push-displacement composition; (2) permitting the aqueous fluid to dissolve the gelatin capsule in the dosage form; (3) letting imbibed fluid mix with the emulsifiable formulation to form a dispensable emulsion; and (4) letting imbibed fluid cause the push-displacement layer to expand and push the emulsified formulation through an orifice at a controlled rate over a sustained release period up to 24 hrs. for therapy.

Inasmuch as the foregoing specification comprises preferred embodiments of the invention, it is understood that variations and modifications may be made herein, in accordance with the inventive principles disclosed, without departing from the scope of the invention.

What is claimed is:

1. A sustained release dosage form, comprising:
   a capsule made of a thermoplastic polymer composition having a softening point below 200° C. and an orifice formed or formable within the capsule wherein the capsule contains components consisting essentially of:
   (a) a self-emulsifying formulation contained within a first portion of the capsule in contact with the orifice, the formulation comprising a drug, an emulsifying surfactant, and an oil; and
   (b) in an expandable composition contained within a second portion of the capsule separated from the orifice, by the self-emulsifying formulation of (a),
   wherein there is no layer separating the self-emulsifying formulation from the expandable composition,
   wherein the expandable composition is configured to expand and expel the self-emulsifying formulation through the orifice.

2. The sustained release dosage form of claim 1, wherein the expandable composition comprises in combination an osmopolymer, an osmotically effective solute, and a poly (cellulose) selected from the group consisting of hydroxyethylcellulose, hydroxypropylcellulose, hydroxypropylmethylcellulose, and hydroxypropylbutylcellulose.

3. The sustained release dosage form of claim 1, wherein the drug comprises a progestin or an estrogen.

4. The sustained release dosage form of claim 1, wherein the oil is selected from the group consisting of a vegetable oil, a mineral oil, an animal oil, a marine oil, an ester of an unsaturated fatty acid, a monoglyceride, a diglyceride, a triglyceride, an acetylated glyceride, olein, palmitin, stearin, lauric acid hexylester, oleic acid, oleylester, glycolyzed ethoxylated glycerides of oils, fatty acids comprising 13 molecules of ethyleneoxide, and oleic acid decylester.

5. The sustained release dosage form of claim 1, wherein the oil is an acetylated glyceride and the surfactant is a polyoxyethylenated castor oil comprising 9 to 52 moles of ethylene oxide.

6. The sustained release dosage form of claim 1, wherein the emulsifying surfactant is selected from the group consisting of polyoxyethylenated castor oil, polyoxyethylene lauryl ether, polyoxyethylenated stearic acid, polyoxyethylenated stearyl alcohol, and polyoxyethylenated oleyl alcohol.

7. The sustained release dosage form of claim 1, where the capsule is an injection-molded capsule.

8. The sustained release dosage form of claim 1, further comprising a semipermeable wall formed over at least a portion of an outer surface of the capsule.

9. The sustained release dosage form of claim 8, further comprising an orifice formed or formable within the semipermeable wall.

10. The sustained release dosage form of claim 1,
wherein the emulsifying surfactant is selected from the group consisting of polyoxyethylenated castor oil, polyoxyethylene lauryl ether, polyoxyethylenated stearic acid, polyoxyethylenated stearyl alcohol, and polyoxyethylenated oleyl alcohol, and wherein the oil is selected from the group consisting of a monoglyceride, a diglyceride, a mixture of mono- and diglycerides of 16 to 18 carbons, and an acetylated glyceride.

11. The sustained release dosage form of claim 10, wherein the expandable composition comprises in combination, an osmopolymer, an osmotically effective solute, and a poly(cellulose) selected from the group consisting of hydroxyethylcellulose, hydroxypropylcellulose, hydroxypropylmethylcellulose, and hydroxypropylbutylcellulose.

12. The sustained release dosage form of claim 10, wherein the oil is an acetylated glyceride and the emulsifying surfactant is a polyoxyethylenated castor oil comprising 9 to 52 moles of ethylene oxide.

13. The sustained release dosage form of claim 10, wherein the drug comprises a progestin or an estrogen.

14. The sustained release dosage form of claim 10, wherein the capsule is made of a thermoplastic polymer composition having a softening point below 200° C.

15. The sustained release dosage form of claim 10, where the capsule is an injection-molded capsule.

16. The sustained release dosage form of claim 10, further comprising a semipermeable wall formed over at least a portion of an outer surface of the capsule.

17. The sustained release dosage form of claim 16, further comprising an orifice formed or formable within the semipermeable wall.

\* \* \* \* \*